United States Patent [19]

Miyagawa et al.

[11] Patent Number: 5,281,531
[45] Date of Patent: Jan. 25, 1994

[54] HOST AND VECTOR FOR PRODUCING D-RIBOSE

[75] Inventors: Kenichiro Miyagawa; Naoyuki Kanzaki, both of Osaka; Junichi Miyazaki, Ibaraki, all of Japan

[73] Assignee: Takeda Chemical Industries, Ltd., Osaka, Japan

[21] Appl. No.: 844,295

[22] Filed: Feb. 28, 1992

[30] Foreign Application Priority Data

Mar. 1, 1991 [JP] Japan .................. 3-036129
Jan. 21, 1992 [JP] Japan .................. 4-008696

[51] Int. Cl.$^5$ .................. C12N 1/21; C12N 15/54; C12N 15/74
[52] U.S. Cl. .................. 435/252.31; 435/320.1; 536/23.2
[58] Field of Search .................. 435/105, 252.31, 320.1; 536/27

[56] References Cited

U.S. PATENT DOCUMENTS 3,970,522  7/1976  Sasajima et al. .................. 435/105

FOREIGN PATENT DOCUMENTS 0412688  2/1991  European Pat. Off. .

OTHER PUBLICATIONS

Fujita et al. (1986), J. Biol. Chem. 261(29): 13744–13753.
Fujita et al. (1987), Proc. Nat. Acad. Sci USA 84: 4524–4528.
Lehninger (1982), Principles of Biochemistry, Worth Publishers Inc. (New York), pp. 456–457.
K. Sasajima et al., Carbohydrate Metabolism-Mutants of a Bacillus Species from Agricultural & Biological Chemistry, vol. 35, pp. 509–517 (1971).

Primary Examiner—Richard A. Schwartz
Assistant Examiner—Philip W. Carter
Attorney, Agent, or Firm—David G. Conlin; Ronald I. Eisenstein

[57] ABSTRACT

Disclosed are (1) a method of producing D-ribose which comprises cultivating a microorganism belonging to the genus Bacillus having D-ribose producing ability in a medium, the microorganism belonging to the genus Bacillus containing a DNA sequence participating in expression of a gluconate operon which is partly or wholly modified so as to highly express the gluconate operon in the microorganism belonging to the genus Bacillus, accumulating D-ribose, and collecting D-ribose thus obtained; (2) a novel microorganism belonging to the genus Bacillus having D-ribose producing ability transformed with DNA which contains a DNA sequence participating in expression of a gluconate operon which is partly or wholly modified so as to highly express the gluconate operon in the microorganism belonging to the genus Bacillus; (3) novel DNA in which a promoter of a gluconate operon of a microorganism belonging to the genus Bacillus is modified so as to highly express said gluconate operon in the microorganism belonging to the genus Bacillus; and (4) a novel vector into which DNA is introduced in which a promoter of a gluconate operon of a microorganism belonging to the genus Bacillus is modified so as to highly express the gluconate operon in the microorganism belonging to the genus Bacillus, whereby D-ribose can be produced in stable form in large amounts.

16 Claims, 4 Drawing Sheets

HOST AND VECTOR FOR PRODUCING D-RIBOSE

BACKGROUND OF THE INVENTION

The present invention relates to a method of producing D-ribose by fermentation, and more particularly to a method of producing D-ribose using microorganisms belonging to the genus Bacillus modified by recombinant DNA technology so as to produce D-ribose efficiently.

D-ribose is contained in all organisms as a constituent component of ribonucleic acid, and ribitol, a reduced derivative thereof, is also contained as a constituent composition of vitamine $B_2$ or ribitol teichonate constituting cell walls. This substance is therefore physiologically very important.

On the other hand, D-ribose has previously been used as a raw material for synthesis of vitamin $B_2$, and has also recently been used as a raw material for synthesis of nucleic acid flavor enhancers. It is therefore industrially significant to prepare D-ribose at low cost and on a large scale.

The production methods of D-ribose hitherto known include the methods of extracting and isolating from natural products, the methods of synthesizing using furan, glucose, etc. as raw materials, and the fermentation methods using microorganisms (Japanese Patent Publication Nos. 47-7948/1972, 50-16878/1975, 51-7753/1976, 52-3/1977, 58-17591/1983 and 59-26276/1984).

On the other hand, enzymes such as gluconate permease involved in the permeation of gluconate in cells and gluconokinase producing 6-phosphogluconate from gluconate are present in *Bacillus subtilis*. These enzymes are coded for by a gene called gluconate operon. The gluconate operon (gnt operon) consists of four regions, gntR, gntK, gntP and gntZ [Y. Fujita et al., *J. Biol. Chem.*, 261, 13744-13753 (1986)]. The expression of these enzymes is regulated by the expression regulating region (gntR) which is located adjacently upstream from the structural genes (gntK and gntP) coding for these enzymes [Y. Fujita et al., *Pro. Natl. Acad. Sci. U.S.A.*, 84, 4524-4528 (1987)]. However, this document does not suggest the relationship to D-ribose producing ability at all.

All of the above-mentioned methods for producing D-ribose have disadvantages in that the production processes are complicated, in that the raw materials are expensive, or in that the yield is lowered by production of gluconate as a by-product. They are therefore not always satisfactory as industrial production methods for D-ribose at low cost. For this reason, a more advantageous method for producing D-ribose has been desired.

SUMMARY OF THE INVENTION

In view of such a present situation, the present inventors studied methods using microorganisms, and particularly screened factors participating in the efficient production of D-ribose by fermentation using microorganisms belonging to the genus Bacillus. The results revealed that D-ribose was produced not only by the usual pentose phosphate pathway through glucose-6-phosphate, but also by the gluconate pathway, in the microorganisms belonging to the genus Bacillus having D-ribose producing ability. Namely, the present inventors considered that gluconate was phosphorylated with gluconokinase to produce 6-phosphogluconate and D-ribose was produced therefrom through the pentose phosphate pathway in order to accumulate it.

As a result of further studies, the present inventors have discovered that it is important for the excess production of D-ribose to highly express the gluconate operon (gnt operon) coding for gluconokinase and gluconate permease, enzymes which are important for conversion from gluconate to D-ribose, in the production of D-ribose by fermentation using the microorganism belonging to the genus Bacillus.

Although the gluconate operon is known to have the region regulating the expression of the gene as described above, the present inventors have discovered that not only the gntR exists as such a region, but also a promoter has an important role in the regulation. The present inventors have further discovered that D-ribose can be stably produced in large amounts by modifying the promoter as well as the gntR in a structure by which the high expression is expected, preparing a novel DNA fragment having the structural genes for gluconokinase and gluconate permease located downstream thereof, transforming a microorganism belonging to the genus Bacillus having D-ribose producing ability using this DNA fragment to obtain a novel microorganism which highly expresses the gluconate operon, and cultivating the resulting microorganism.

The present invention was completed based on such discoveries. The present invention provides (1) a method of producing D-ribose which comprises cultivating a microorganism belonging to the genus Bacillus having D-ribose producing ability in a medium, the microorganism belonging to the genus Bacillus containing a DNA sequence participating in expression of a gluconate operon which is partly or wholly modified so as to highly express the gluconate operon in the microorganism belonging to the genus Bacillus, accumulating D-ribose, and collecting D-ribose thus obtained; (2) a novel microorganism belonging to the genus Bacillus having D-ribose producing ability transformed with DNA, the DNA contains a DNA sequence participating in expression of a gluconate operon and being partly or wholly modified so as to highly express the gluconate operon in the microorganism belonging to the genus Bacillus; (3) novel DNA in which a promoter of a gluconate operon of a microorganism belonging to the genus Bacillus is modified so as to highly express said gluconate operon in the microorganism belonging to the genus Bacillus; and (4) a novel vector into which a DNA is introduced, in the DNA a promoter of a gluconate operon of a microorganism belonging to the genus Bacillus is modified so as to highly express the gluconate operon in the microorganism belonging to the genus Bacillus.

DESCRIPTION OF THE PREFERRED EMBODIMENTS

Figures 1A, 1B:
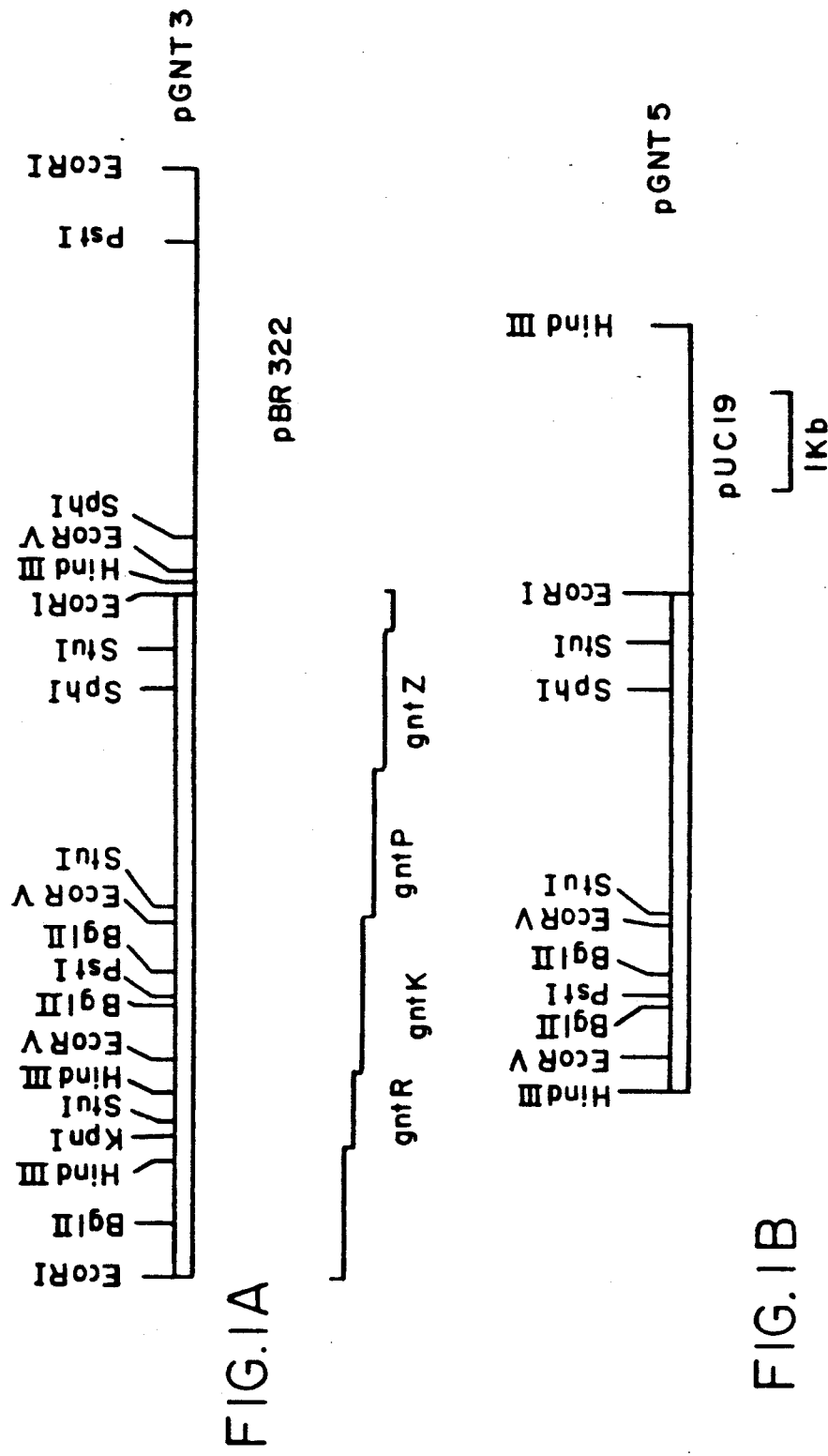
FIGS. 1(a) and 1(b) are restriction enzyme maps of plasmid pGNT3 obtained in Example 1 (2) and plasmid pGNT5 obtained in Example 1 (3), respectively, wherein each open box indicates an inserted fragment, each solid line portion indicates a vector, and gene symbols gntR, gntK, gntP and gntZ indicate positions corresponding to four open reading frames of a gluconate operon in the inserted fragment.

When the DNA sequence participating in the expression of the gluconate operon is partly or wholly modified in the present invention, the gntR or an expression regulating region located upstream from an open reading frame coding for gluconokinase of the gluconate operon, and/or the promoter is modified. Specifically, the modification of the gntR includes deletion of the gntR or inactivation by insertion of other DNA(s) into the gntR. Although this gntR has a region participating in expression regulation by glucose and a DNA region participating in expression induction by gluconate, either of them may be deleted or inactivated.

On the other hand, the modification of the promoter of the gluconate operon may include, for example, a replacement of the promoter with another gene expressible in the microorganism belonging to the genus Bacillus for the promoter of the gluconate operon. Specifically, the promoter of the gluconate operon is substituted by a promoter derived from the chromosomal DNA of the microorganism belonging to the genus Bacillus or a promoter derived from a phage of the microorganism belonging to the genus Bacillus as described below.

The modification of the DNA sequence in the present invention includes the modification of the gntR and/or the modification of the promoter. It is however most preferred that both modifications are conducted together.

It is desirable that the gluconate operon-containing DNA used in the present invention contains the entire DNA of the operon and some peripheral regions upstream and downstream thereof. However, the DNA may contain a 5'-terminal portion of the operon DNA or a 5'-terminal portion of the operon DNA and a region upstream therefrom. The DNA is easily isolated from the chromosomal DNA of microorganisms by cloning using recombinant DNA techniques. For example, an *Escherichia coli* host-vector system and a *Bacillus subtilis* host-vector system are used.

A donor of the DNA containing the gluconate operon is not necessarily required to have D-ribose producing ability. There is no particular restriction on its source as a general rule and any microorganism may be used as the donor, as long as a nucleotide sequence of a gluconate operon of the donor strain has high homology with a nucleotide sequence of a gluconate operon on a chromosome of a microorganism belonging to the the genus Bacillus used as a recipient having D-ribose producing ability described below. In particular, the use of microorganisms belonging to the genus Bacillus is preferred from the viewpoint of treatment, and the resulting transformant is expected to be stable.

Such DNA donors include microorganisms belonging to the genus Bacillus such as *Bacillus subtilis* and *Bacillus pumilus*. Examples thereof include the following strains:

*B. subtilis* No. 168 (BGSC IA1)
*B. subtilis* No. 115 (IFO 14187, FERM BP-1327)
*B. subtilis* MI114 (Gene, 24, 255 (1983))
BGSC: The Bacillus Genetic Stock Center
IFO: The Institute for Fermentation, Osaka, Japan As methods for preparing chromosomal DNA from donors, known methods such as the method of extracting chromosomal DNA by use of phenol (H. Saito and K. Miura, *Biochim. Biophy. Acta*, 72, 619) can be used. The chromosomal DNA thus obtained is digested with a restriction enzyme appropriately selected, and ligated to a vector by using DNA ligase. A gluconate assimilation deficient host bacterium is transformed with the resulting ligation mixture, and a transformant complemented in that deficiency is selected, whereby gluconate operon-containing DNA can be obtained. Also, the gluconate operon-containing DNA can be cloned by colony hybridization methods or plaque hybridization methods using a DNA oligomer which is a portion of the known *Bacillus subtilis* gluconate operon nucleotide sequence [Y. Fujita et al., *J. Biol. Chem.*, 261, 13744–13753 (1986)] as a probe. When the host bacterium is *Escherichia coli*, it can be transformed according to known methods such as the method of S. N. Cohen et al. (*Pro. Natl. Acad. Sci. U.S.A.*, 69, 2110).

The DNA containing the gene can be obtained in large amounts from the transformant thus obtained, according to the method described in T. Maniatis et al., *Molecular Cloning*, 2nd edition, 1.33–1.52, Cold Spring Harbor Laboratory Press (1989).

In order to produce the novel DNA of the present invention from the gluconate operon-containing DNA thus obtained, the use of recombinant DNA techniques is convenient. For example, the DNA of the present invention can be prepared and isolated by procedures briefly described below, using the *E. coli* host-vector system.

In the course of the preparation of the DNA of the present invention in *E. coli* hereinafter described, a DNA fragment is often subcloned to another vector or bound thereto by use of a polylinker. For this purpose, it is convenient also for the preparation of the novel DNA or the determination of the nucleotide sequence to subclone the DNA fragment, utilizing, for example, a polylinker portion of *E. coli* vector pUC118 or pHSG398.

The region participating in the expression regulation of the gluconate operon is removed from the plasmid containing the gluconate operon using an appropriate enzyme, and an enzyme having exonuclease activity which digests a double stranded DNA from the terminus thereof in turn, for example, BAL31, as so desired. More specifically, the region upstream from the 5'-terminal side of the open reading frame coding for gluconokinase is removed by cleavage, and a ribosome binding site, a sequence participating in binding of the mRNA to the 16S ribosome RNA from a microorganism belonging to the genus Bacillus, is ligated to the 5'-flanking region of an initiation codon of the open reading frame, adjusting the direction. A promoter sequence is further ligated upstream from the 5'-terminal side thereof, whereby the DNA of the present invention can be obtained. When the promoter sequence is ligated, it is preferred to ligate a promoter sequence having promoter activity highly expressible in the microorganism belonging to the genus Bacillus other than the gluconate operon promoter.

As the ribosome binding site, DNA cloned from the microorganisms belonging to the the genus Bacillus and synthetic DNA may be used, as long as they have a sequence complementing 3'OHUCUUUCCUCC5' (SEQ ID NO: 1), a messenger RNA binding site of 16S ribosome of the microorganism belonging to the genus Bacillus having D-ribose producing ability described below. DNA located upstream from the openreading frame of gluconokinase in the above-mentioned clone also may be used. In this case, in order to remove the region participating in the expression regulation of the gluconate operon exactly, the kind of each restriction enzyme used, the amount of the enzyme having exonuclease activity and the reaction time are varied, thereby obtaining various DNA fragments different in the kind and size of the deleted portions. A desired DNA fragment may be selected from these fragments by appropriate means as described below, for example, based on the results of the nucleotide sequence determination of the fragments. After the DNA fragment is subcloned into a vector used for the nucleotide sequence determination, such as M13, pUC118 or pHSG398, the nucleotide sequence can be determined by known methods such as the method of F. Sangar et al. (*Proc. Natl. Acad. Sci. U.S.A.*, 74, 5463).

Any promoter sequence may be used as long as it has a DNA sequence expressible in the microorganisms belonging to the genus Bacillus having D-ribose producing activity used below, and it does not matter whether it is derived from procaryotes, eucaryotes or synthetic DNA.

Examples of such promoters include promoters derived from chromosomal DNA of microorganisms belonging to the genus Bacillus, promoters derived from phages of microorganisms belonging to the genus Bacillus and promoters derived from plasmids autonomously replicating in microorganisms belonging to the genus Bacillus.

Specific examples of such promoters include
AAAAGGTATTGACTTTCCCTACAGGGTGT-GTAATAATTTATATACA, SPO1-15 (SEQ ID NO: 2)

AAAAGTTGTTGACTTTATCTACAAGGTGTG-GCATAATAATCTTAAC, SPO1-26 (SEQ ID NO: 3);

GAAAAGTGTTGAAAATTGT CGAACAGGGT-GATATAATAAAGAGTA, φ29G3b (SEQ ID NO: 4);

GAAAAGGGTAGACAAACTATCGTT-TAACATGTTATACTATAATAGAA, φ 29G2 (SEQ ID NO: 5);

ATTAATGTTTGACAACTAT TACAGAGTATG-CTATAATGGTAGTATC, φ 29A1 (SEQ ID NO: 6);

TAATATCGTTGACATTATCCATGTCCGTTGT TAAGATAAACATGAA, pur operon (SEQ ID NO: 7);

CCGCTTCCTTGACATGCTCTTGGCTAGTT-GATAATCAACATATAAT, gua B (SEQ ID NO: 8); and

AAAACATTTACTCCATGGAAAATGAT-GATAGATTAATTTTTAA, PI (SEQ ID NO: 9).

These promoters can be cut out of DNA fragments (plasmids) containing the promoters by use of appropriate restriction enzymes, and fractionated, for example, on agarose gel electrophoresis or polyacrylamide gel electrophoresis, followed by recovery to use them. DNAs having nucleotide sequences of the above-mentioned promoters can also be synthesized by the phosphoamidide method using commercial DNA synthesizers (for example, a synthesizer manufactured by Applied Biosystems) according to the protocols thereof.

Thus, the DNAs of the present invention are prepared and employed in transformation of microorganisms belonging to the genus Bacillus. It is sometimes convenient to ligate marker genes expressible in microorganisms belonging to the genus Bacillus, such as drug resistant genes, to the DNAs of the present invention, when transformants of the microorganisms belonging to the genus Bacillus are selected as described below.

In this case, it is convenient to ligate a portion of the 5'-adjacent region of the gluconate operon upstream from the 5'-terminus of the bound promoter, because double crossover type recombination takes place when recombination is conducted on a chromosome of the microorganism belonging to the genus Bacillus having D-ribose producing activity as described below.

Then, in order to obtain the DNA of the present invention in large amounts, the host strain belonging to the *E. coli* is transformed using the above-mentioned resulting solution in which ligation is performed by T4 DNA ligase. When drug resistance is used as a selective marker, a strain is grown in a selective medium and the medium containing the drug is obtained. The DNA of the present invention can be obtained from the transformant thus obtained, according to the method described in *Molecular Cloning*, 2nd edition, 1.33–1.52 mentioned above.

Methods for transforming the microorganisms belonging to the genus Bacillus having D-ribose producing ability with the novel DNA thus obtained to prepare novel microorganisms are hereinafter described.

The microorganisms belonging to the genus Bacillus having D-ribose producing ability may belong to any species of Bacillus. For example, bacteria belonging to *B. subtilis* or *B. pumilus* are preferably used. Most preferred are Bacteria belonging to *B. subtilis*.

In order to produce D-ribose effectively by the present invention, it is preferred that these D-ribose producing bacteria have gluconate producing ability but strains which have too great an ability to produce gluconate accumulate a large amount of gluconate in media and the strains cannot therefore be expected to produce D-ribose effectively. However, when the strains are transformed with the DNA of the present invention, gluconate is converted to D-ribose. For this reason, D-ribose can be effectively accumulated without production of gluconate as a by-product. Conversely, when strains not having gluconate producing ability are used, the strains can be easily induced to strains having gluconate producing ability by enhancing 2-deoxy-D-glucose oxidation activity or by expressing the glucose dehydrogenase gene of the strains using cloned glucose dehydrogenase gene of *B. subtilis* (K. A. Lampel et al., *J. Bacteriol.*, 166. 238–243). It is possible for these strains to carry out the present invention. For example, if one or more known properties which are considered to be advantageous to the production and accumulation of D-ribose, such as the deficiency in at least one of transketolase and D-ribulose-5-phosphate-epimerase and the deficiency of sporogenous ability, are further added to these strains to use them as D-ribose producing bacteria, more suitable results can be obtained to improve the productivity of D-ribose in many cases.

Typical examples of microorganisms belonging to the genus Bacillus having D-ribose producing ability include the following strains:
*B. subtilis* No. 429 (IFO 12603, ATCC21359) *1
*B. subtilis* No. 483 (IFO 12604, ATCC21360) *1
*B. subtilis* No. 608 (IFO 13323, FERM P-1490) *2
*B. subtilis* No. 957 [IFO 13565, FERM P-2259) *3
*B. subtilis* No. 941 (IFO 13573, FERM P-2360) *3
*B. subtilis* No. 1054 (IFO 13586, FERM P-2467) *3
*B. subtilis* No. 1067 (IFO 13588, FERM P-2468) *3
*B. subtilis* No. 1097 (IFO 13621, FERM P-2833) *3, 4
*B. subtilis* TK 103 (IFO 15138, FERM BP-3290)
*B. pumilus* No. 503 (IFO 12600, ATCC21356) *1
*B. pumilus* No. 537 (IFO 12601, ATCC21357) *1
*B. pumilus* No. 558 (IFO 12602, ATCC21358) *1
*B. pumilus* No. 716 (IFO 13322, FERM BP-812) *2
*B. pumilus* No. 911 (IFO 13566, FERM P-2260) *3
*B. pumilus* No. 1027 (IFO 13585, FERM P-2466) *3
*B. pumilus* No. 1083 (IFO 13620, FERM P-2832) *3, 4

*1: Japanese patent publication No. 47-7948/1972, U.S. Pat. No. 3,607,648
*2: Japanese Patent Publication No. 50-16878/1975, U.S. Pat. No. 3,919,046
*3 Japanese patent publication No. 51-7753/1976, Japanese Patent Publication No. 52-1993/1977, U.S. Pat. No. 3,970,522
*4: Japanese Patent Publication No. 58-17591/1983

In the present invention, the novel DNA which is the chromosomal DNA containing the DNA sequence participating in the expression of the gluconate operon of the microorganism belonging to the genus Bacillus and the 3'-adjacent region of that sequence, the DNA sequence participating in the expression of the gluconate operon being partly or wholly modified so as to highly express the gluconate operon in the microorganism belonging to the genus Bacillus, is used for the transformation of the microorganism belonging to the genus Bacillus having D-ribose producing ability. In this case, the DNA of the present invention can be used in the state that the DNA is introduced into a plasmid. It is also possible to use linear DNA obtained by cleaving the plasmid or the DNA cut out of the plasmid. To obtain DNA fragments, the transformation can be accomplished either by using said DNA fragments or by using a vector containing said DNA fragments. Using the DNA fragments, the microorganisms belonging to the genus Bacillus can be transformed by known methods such as the method described in C. Anagnostopoulos and J. Spizizen, *J. Bacteriol.*, 81, 741 (1961).

For example, when the drug tolerance gene is used as the selective marker, the selection of the transformant can be easily carried out using an agar plate containing the corresponding drug.

It can be easily determined by the assay of gluconokinase activity whether or not the transformant thus obtained is a novel microorganism having desired characteristics. Namely, the microorganism transformed with the DNA of the present invention which is derepressed and enhanced in the expression of the gluconate operon has higher gluconokinase activity than the parent strain thereof. Because of its high gluconokinase activity, the D-ribose accumulating ability of the transformed microorganisms is higher than that of the parent strain.

Typical examples of such transformants of the present invention include *B. subtilis* RS101 (IFO 15138, FERM BP-3291) obtained in Example 2 described below.

Of course, various transformants can be easily prepared in a similar manner by selecting the promoters or the microorganisms belonging to the genus Bacillus according to the methods desired in this specification.

Using the transformants obtained in the present invention, D-ribose is prepared by methods similar to the conventional methods for cultivating D-ribose producing bacteria. Namely, various nutrients such as carbon sources and nitrogen sources are used as media. Examples of carbon sources include D-glucose, D-mannose, D-sorbitol, D-mannitol, sucrose, molasses, starch hydrolysates, starch, acetic acid and ethanol.

The nitrogen sources used include organic nitrogen compounds such as urea and amino acids, as well as corn steep liquor, cotton seed meal, yeast extract, dry yeast, fish meal, meat extract, peptone, Casamino acids, and inorganic nitrogen compounds such as aqueous ammonia, gaseous ammonia, ammonium sulfate, ammonium nitrate, ammonium chloride, ammonium carbonate, ammonium phosphate and sodium nitrate. Corn steep liquor is advantageously used among others.

In addition to these carbon sources and nitrogen sources, various metals, vitamins, amino acids, etc. necessary for growth of the microorganisms used are appropriately added to the media.

Cultivation is usually conducted under aerobic conditions such as submerged culture in a flask with shaking or in a fermentor with aeration and agitation.

There is no particular restriction on cultivation conditions, namely the cultivation temperature, the pH of the media and the cultivation time. However, the cultivation temperature is generally about 18° to about 45° C., and preferably about 25 to about 40° C.

The pH of the media is generally about 4.5 to about 9, and preferably about 5.5 to about 8. The cultivation time is generally about 18 to about 180 hours, and preferably about 36 to about 120 hours. In order to collect the accumulated D-ribose from the culture solutions, separation and purification methods of D-ribose known in the art are employed. For example, the cells are removed by filtration or centrifugation of the culture solution. Then, the solution from which the cells are removed is decolorized and desalted by activated charcoal treatment or ion exchange resin treatment, followed by concentration. A solvent such as ethyl alcohol is added to the concentrated solution to crystallize and obtain D-ribose.

According to the present invention, the D-ribose producing bacteria of genus Bacillus having gluconate producing ability are transformed using the novel DNA which is the chromosomal DNA containing the DNA sequence participating in the expression of the gluconate operon of the microorganism belonging to the genus Bacillus and the 3'-adjacent region of that sequence, the DNA sequence participating in the expression of the gluconate operon being partly or wholly modified so as to highly express the gluconate operon in the microorganisms belonging to the genus Bacillus. The gluconate operon coding for gluconokinase, etc. which are enzymes important for conversion from gluconate to D-ribose is highly expressed and the novel microorganisms having enhanced enzyme activity and D-ribose producing activity can be obtained. By cultivating the novel microorganisms in the media, D-ribose can be prepared in stable form in large amounts without substantial accumulation of gluconate.

When nucleotides and so on are indicated by abbreviations in the specification and drawings, the abbreviations adopted by the IUPAC-IUB Commission on Biochemical Nomenclature or commonly used in the art are employed. For example, the following abbreviations are used.

DNA: Deoxyribonucleic acid
A: Adenine
T: Thymine
G: Guanine
C: Cytosine
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: ethylenediaminetetraacetic acid The present invention will be described in more detail with the following Examples. It is understood of course that these Examples are not intended to limit the scope of the invention.

B. subtilis No. 115 used in Example 1 (1) described below was deposited with the Institute for Fermentation, Osaka, Japan (IFO) under the accession number IFO 14187 on Jul. 13, 1982, and with the Fermentation Research Institute, the Agency of Industrial Science and Technology, the Ministry of International Trade and Industry, Japan (FRI) under the accession number FERM BP-1327 on Mar. 28, 1987.

Transformants B. subtilis TK103 and B. subtilis RS101 obtained in Example 2 described below were deposited with the Institute for Fermentation, Osaka, Japan (IFO) under the accession numbers IFO 15138 and IFO 15139 on Feb. 14, 1991, and with the Fermentation Research Institute, the Agency of Industrial Science and Technology, the Ministry of International Trade and Industry, Japan (FRI) under the accession numbers FERM BP-3290 and FERM BP-3291 on Feb. 21, 1991.

The Examples described below were carried out according to the following processes (1) to (8) unless otherwise indicated.

(1) Digestion of DNA by Restriction Enzyme

Using a restriction enzyme (Takara Shuzo) in an amount of 10 units/$\mu$g of DNA and a buffer solution for the restriction enzyme recommended by the manufacturer of the enzyme, digestion was conducted at the temperature of 60° C. for 60 minutes. Subsequently, extraction was carried out with phenol saturated with TE buffer [10 mM Tris-HCl (pH 7.5), 1 mM EDTA]. Then, 1/10 volume of 3M sodium acetate (pH 6) was added to the extract, and 2.5 volumes of ethanol was further added thereto, followed by centrifugation to recover DNA.

(2) Large Scale Preparation of Plasmid

Extraction was carried out according to the method described in *Molecular Cloning*, 1.33–1.52. Namely, 250 ml of LB medium (10 g/l bactotryptone, 5 g/l yeast extract, 5 g/l sodium chloride) was inoculated with *E. coli* containing the plasmid DNA. After cultivation was conducted overnight, the cells were harvested and washed. Then, lysozyme was added to the washed cells, and a 0.2N solution of sodium hydroxide containing 1% sodium lauryl sulfate was further added thereto to lyse the cells. After addition of 5M potassium acetate, a supernatant containing the plasmid was obtained by centrifugation. To the supernatant was added 0.6 volume of isopropanol to precipitate the plasmid DNA. After washing with ethanol, the plasmid DNA was dissolved in TE buffer. Cesium chloride was added thereto to give a specific gravity of 1.60, and ethidium bromide was added thereto to a final concentration of 600 $\mu$g/ml. Using an ultracentrifuge (rotor $V_{65}Ti$), centrifugation was carried out at 20° C. at 50,000 rpm for 12 hours. Plasmid bands detected by ultraviolet rays were collected, and ethidium bromide was removed by extraction using n-butanol, followed by ethanol precipitation.

(3) Transformation of *E. coli*

Transformation was conducted according to the method described in Molecular Cloning, 1.74–1.84.

*E. coli* was inoculated onto 3 ml of LB medium, and cultivated overnight. Then, 1 ml of the resulting culture solution was inoculated onto 100 ml of LB medium, and cultivated at 37° C. with shaking to give a cell amount of about $5 \times 10^7$ cells/ml. Subsequently, the cells are collected, and 50 ml of a sterilized aqueous solution containing 50 mM calcium chloride and 10 mM Tris-HCl (pH 8) cooled with ice was added thereto to suspend the cells. The resulting suspension was cooled with ice for 15 minutes, followed by centrifugation. The centrifuged cells were suspended again in 6.7 ml of the above-mentioned aqueous solution. The DNA was added to 0.2 ml of the resulting suspension, and cooled with ice for 30 minutes. Then, 0.8 ml of LB medium was added thereto, followed by cultivation at 37° C. for 1 hour. The resulting product was applied to an LB agar plate medium containing a drug, and cultivated at 37° C. overnight.

(4) BAL 31 Exonuclease Digestion Treatment

BAL 31 digestion treatment was conducted to digest both strands of the DNA from both termini. Namely, 10 $\mu$g of the DNA treated with the restriction enzyme was dissolved in 100 $\mu$l of BAL 31 buffer (12 mM calcium chloride, 12 mM magnesium chloride, 200 mM sodium chloride, 20 mM Tris-HCl (pH 8), 2 mM EDTA), and 1 unit of BAL 31 exonuclease (Takara Shuzo) was added thereto. After the resulting solution was incubated at 30° C., it was subjected to phenol extraction and ethanol precipitation. Then, the above-mentioned DNA was suspended in 20 $\mu$l of a buffer for T4 DNA polymerase [33 mM Tris-acetate (pH 7.9), 10 mM magnesium acetate, 0.5 mM dithiothreitol, 66 mM potassium acetate, 0.01% BSA, 0.1 mM dATP, 0.1 mM dGTP, 0.1 mM dCTP, 0.1 mM dTTP] to convert cohesive end to flush end with 5 units of T4 DNA polymerase (Takara Shuzo). After the resultant suspension was maintained at a temperature of 37° C. for 30 minutes, it was subjected to phenol extraction and ethanol precipitation.

(5) Ligating Reaction of DNA

Using a DNA ligation kit (Takara Shuzo), two or three kinds of DNA fragments were ligated. Ligation was carried out according to the method specified by the manufacturer.

(6) Transformation of *B. subtilis*

Transformation was performed according to the method of Dubnou et al. Namely, *B. subtilis* was inoculated onto 5 ml of LB medium, and cultivated at 37° C. overnight. Then, 0.5 ml of the resulting product was transferred to 20 ml of SPI medium (1.4% dipotassium phosphate, 0.6% monopotassium phosphate, 0.2% ammonium sulfate, 0.1% sodium citrate, 0.02% magnesium sulfate, 0.5% glucose, 0.02% Casamino acids, 0.1% yeast extract, 50 µg/ml tryptophan, 50 µg/ml leucine), and cultivated at 37° C. for 4 hours. Subsequently, 10 ml of the culture solution was transferred to 100 ml of SPII medium (1.4% dipotassium phosphate, 0.6% monopotassium phosphate, 0.2% ammonium sulfate, 0.1% sodium citrate, 0.02% magnesium sulfate, 0.5% glucose, 75 µg/ml calcium chloride, 508 µg/ml magnesium chloride), and cultivated at 37° C. for 90 minutes. To 1 ml of this cell suspension was added 1 µg of the DNA, followed by shaking at 37° C. for 30 minutes. The resulting product was applied to an LB agar plate medium containing a drug, and cultivated at 37° C. overnight.

(7) Plaque Hybridization

λZAP (Toyobo) in vitro packaged was infected with *E. coli* BB4, and inoculated onto an agar plate to form plaques, and then, a nylon filter (Colony/Plaque Screen NEF-978X, du Pont) was adhered on the agar plate for 3 minutes.

Then, this nylon filter was stripped off from the plate medium, and immersed in a 0.5N aqueous solution of sodium hydroxide for 10 minutes. Subsequently, the filter was immersed in 1M Tris-HCl (pH 7.5) for 10 minutes, followed by drying at room temperature.

On the other hand, a probe was prepared using MEGALABEL (Takara Shuzo) according to the protocol specified by the manufacturer. Hybridization was carried out according to the protocol specified for the nylon filter.

(8) Determination of Nucleotide Sequence

The nucleotide sequence of the DNA was determined using Sequenase (Toyobo) according to the method specified by the manufacturer.

EXAMPLE 1

(1) Preparation of Chromosomal DNA

*B. subtilis* No. 115 [IFO 14187, FERM BP-1327 (deposited on Mar. 28, 1987), (Japanese Patent Publication No. 3-35916/1991, U.S. Pat. No. 4,701,413)] was inoculated onto 40 ml of LB medium, and cultivated at 37° C. overnight, followed by extraction with phenol to obtain 5 mg of chromosomal DNA.

(2) Cloning of Gluconate Operon (gnt Operon)

10 µg of the chromosomal DNA prepared in the preceding item (1) was digested with EcoRI, and the resulting DNA fragments were fractionated by agarose gel electrophoresis. A DNA fragment corresponding to about 7.0 to 8.0 kb was recovered using a unidirectional electroeluter (International Biotechnologies Inc.).

On the other hand, 0.5 µg of λZAP (Toyobo) was digested with EcoRI and mixed with the above-mentioned DNA fragments. After ligation, in vitro packaging was conducted, and *E. coli* BB4 (Toyobo) was infected with the resulting product to form plaques on an agar plate. Using a synthetic oligonucleotide (5'-AGCTACGAAAGCTCATGTCTCGGCGCCTGC-3': SEQ ID NO: 10) as a probe, plaque hybridization was conducted. The in vitro packaging was carried out using Packgene (Seikagaku Kogyo) according to the attached protocol. As a result, DNA was obtained from positive plaques, and a 7.0-kb EcoRI fragment inserted therein was subcloned to the EcoRI site of pBR322 to obtain recombinant plasmid pGNT3 containing the gluconate operon (gntR, gntK, gntP, gntZ). The restriction enzyme map of pGNT3 is shown in FIG. 1(*a*).

(3) Preparation of DNA Fragment from Which a Large Portion of gntR Is Deleted After 5 µg of pGNT3 was double-digested with HindIII and EcoRI, the digested product was applied on agarose gel electrophoresis. Subsequently, a fragment corresponding to 5.0 kb was extracted from the gel, and inserted into the HindIII-EcoRI site of pUC19. Then, *E. coli* JM109 was transformed therewith to ampicillin-resistant strain *E. coli* JM109 (pGNT5), from which plasmid pGNT5 shown in FIG. 1(*b*) was obtained.

Figure 2:
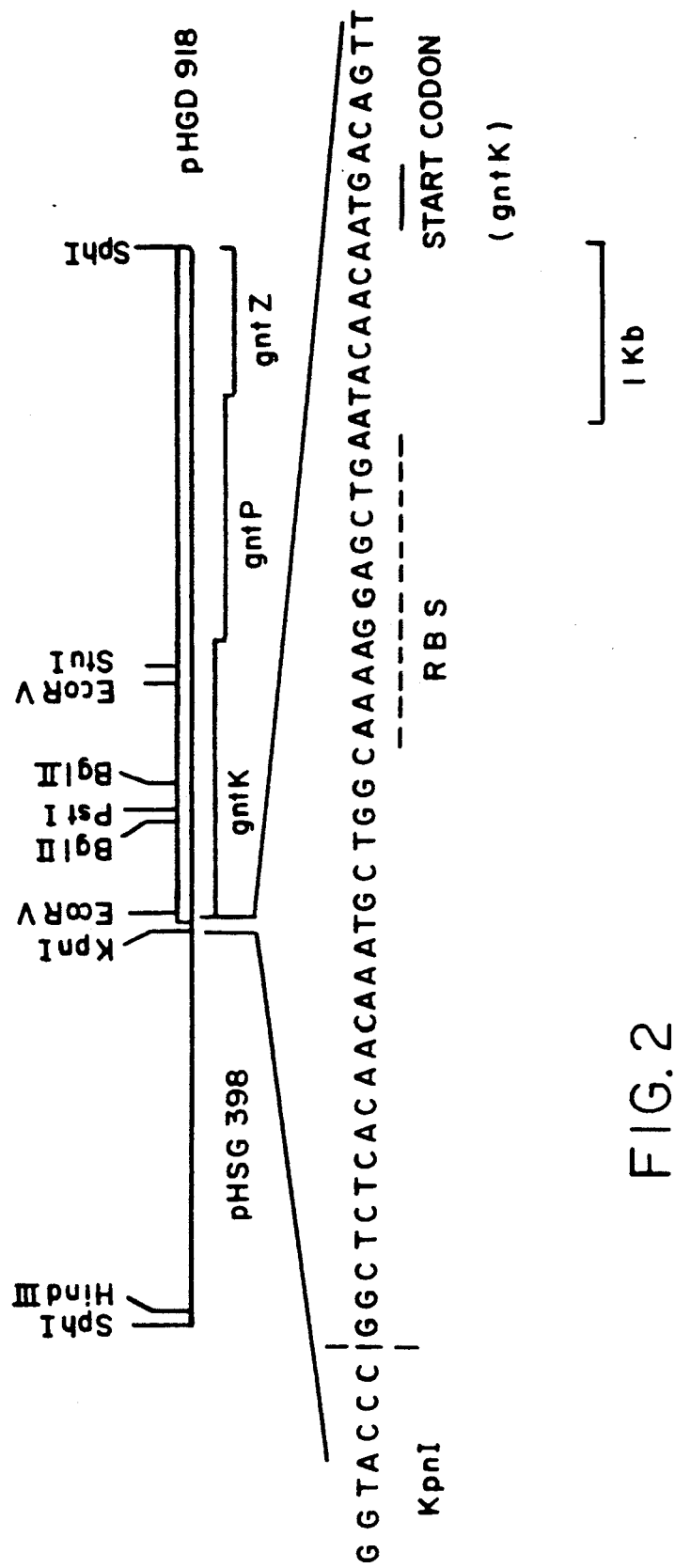
FIG. 2 is a restriction enzyme map of plasmid pHGD918 and a portion of a nucleotide sequence at a binding portion of an inserted fragment and a vector, wherein the vertical dotted line indicates a binding point of the inserted fragment and the vector, the sequence underlined with the dotted line represented as "RBS" indicates a ribosome binding site, and the sequence represented as "start codon" indicates an initiation codon of an open reading frame of the gntK gene.

Subsequently, 10 µg of pGNT5 was digested with HindIII, followed by treatment with BAL31 for 5 minutes. Then, the resulting product was completely digested with SphI to obtain fragments. The fragments were fractionated on agarose gel electrophoresis, and a DNA fragment corresponding to about 3.7 kb was obtained. The DNA fragment thus obtained was ligated to 0.5 µg of pHSG398 (Takara Shuzo) double-digested with SmaI and SphI. Then, *E. coli* JM109 was transformed therewith and a strain resistant to chloramphenicol (30 mg/ml) was selected. As a result, pHGD918 having the structure shown in FIG. 2 was obtained. The determination of the nucleotide sequence confirmed that this plasmid contained all of the gntK gene and the gntP gene and a portion of the gntZ gene of the gluconate operon, but a large portion of the gntR gene was deleted therefrom.

(4) Preparation of Plasmid Containing Gluconate Operon Highly Expressible in microorganisms belonging to the genus Bacillus i) Plasmid pSP19 (European Patent publication No. 412,688) into which an sp promoter was introduced was double-digested with EcoRI and KpnI, and a 0.1-kb fragment was obtained. The fragment was ligated to the EcoRI-KpnI site of plasmid pSKC (European Patent Publication No. 412,688) containing a chloramphenicol acetyltransferase gene, and *E. coli* JM109 was transformed therewith to obtain plasmid pSKCSP from chloramphenicol-resistant strains.

Figure 3:
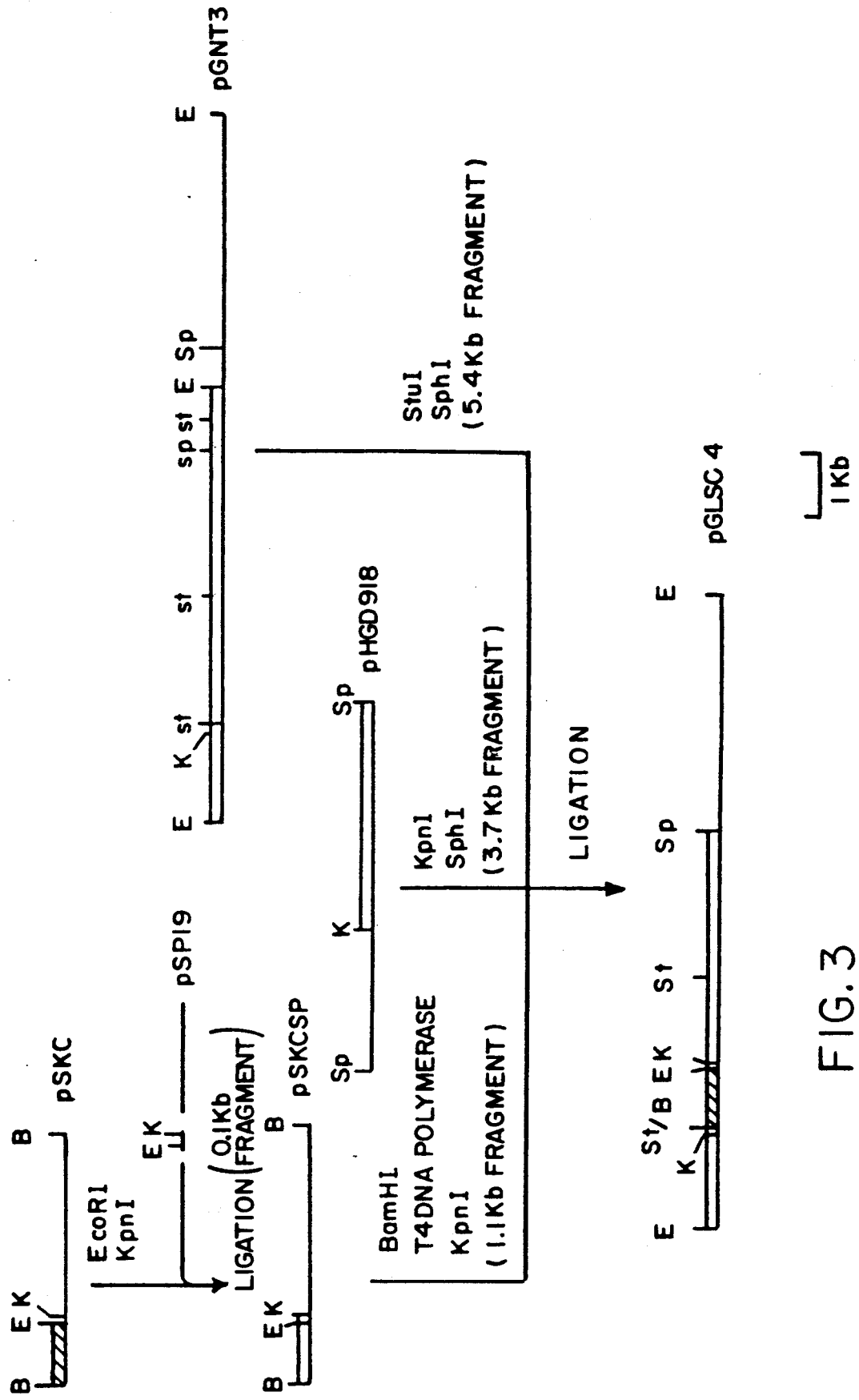
FIG. 3 is a schematic representation showing the construction of plasmid pGLSC4, wherein B, E, K, Sp and St indicate the sites cleaved with restriction enzymes BamHI, EcoRI, KpnI, SphI and StuI, respectively, St/B indicates a binding site where the flush end generated by StuI and the cohesive end generated by BamHI were ligated after being converted to a flush end with T4 DNA polymerase, the open boxes indicate the gluconate operon and regions adjacent thereto, the shaded boxes indicate chloramphenicol acetyltransferase genes, and the black boxes indicate SP promoters.
Figure 4:
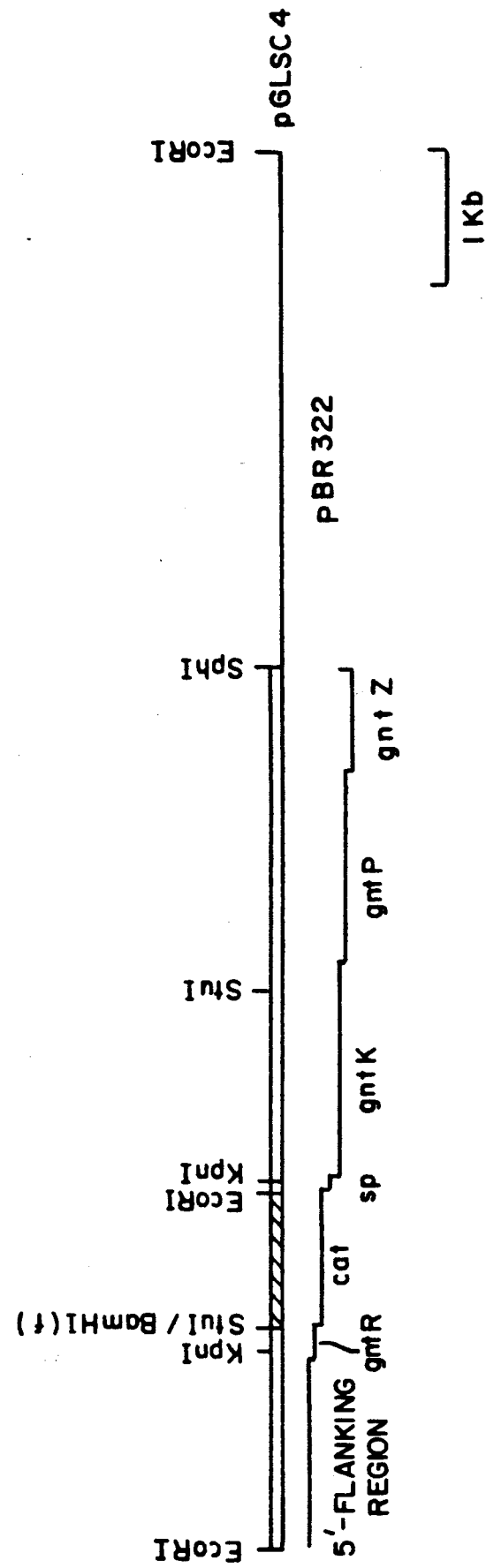
FIG. 4 is a representation showing a restriction enzyme map of plasmid pGLSC4 and a gene locus of the gluconate operon, wherein the open boxes indicate the gnt operon and its 5'-terminal adjacent region, the shaded box indicates a chloramphenicol acetyltransferase gene, the black portion indicates an SP promoter, and the solid line indicates a vector.

Then, 10 µg of pSKCSP was cleaved with BamHI, and thereafter the end of the fragment was rendered flush with T4 DNA polymerase. The resulting product was further cleaved with KpnI, and then subjected to agarose gel electrophoresis to obtain a fragment of about 1.1 kb.

ii) 5 µg of pHGD918 was double-cleaved with KpnI and SphI, and the resulting fragments were fractionated on agarose gel electrophoresis. Then, a fragment of about 3.7 kb was obtained.

iii) Similarly, an StuI-SphI fragment of about 5.4 kb was obtained from pGNT3.

iV) Three fragments obtained in i), ii) and iii) described above were mixed and ligated to one another, and *E. coli* JM109 was transformed therewith to obtain ampicillin-resistant strain *E. coli* JM109 (pGLSC4). Plasmid pGLSC4 was extracted from that strain. The preparation method of pGLSC4 is shown in FIG. 3, and the detailed structure of pGLSC4 is shown in FIG. 4.

pGLSC4 a is recombinant plasmid which contains all of the gntK gene and the gntP gene and a portion of the gntZ gene of the gluconate operon, from which a large portion of gntR considered to participate in their expression regulation is deleted, and which has an SP promoter 5'-upstream from gnt.

EXAMPLE 2

Preparation of Transformant of microorganism belonging to the genus Bacillus in Which Gluconate Operon Is Highly Expressed Using *B. subtilis* No. 115 (IFO 14187, FERM BP-1327) (Japanese Patent Publication No. 3-35916/1991, U.S. Pat. No. 4,701,413) as a parent strain, mutation treatment was conducted with N-methyl-N'-nitro-N-nitrosoguanidine according to the method of Sasajima et al. [*Agric. Biol. Chem.*, 34, 381 (1970); ibid., 35, 509 (1971)] and the method described in Japanese Patent Publication No. 52-1993/1977 (U.S. Pat. No. 3,970,522). Then, using the known replica plate method, mutant *B. subtilis* TK103 (IFO 15138, FERM BP-3290) having shikimic acid requirement and high 2-deoxy-D-glucose oxidation activity was obtained. This mutant has D-ribose producing activity. Then, 10 μg of PGLSC4 obtained in Example 1 was completely digested with SphI to linear DNA. Using this DNA, *B. subtilis* TK103 was transformed to obtain resistant strains to chloramphenicol (10 μg/ml). One of the resistants was named *B. subtilis* RS101 (IFO 15139, FERM BP-3291). This strain was cultivated in a medium containing glucose as a carbon source, and its gluconokinase activity was assayed. As a result, the activity of forming 75 nmol/mg of protein in the cell free extract/minute of 6-phosphogluconate was observed. When the gluconokinase activity of *B. subtilis* TK103 was assayed under the same conditions, the activity of only 0.3 nmol/mg of protein in the cell free extract/minute of 6-phosphogluconate was observed. The gluconokinase activity was assayed according to the method of J. Nishida and Y. Fujita [*Biochim. Biophys. Acta*, 798, 88-95 (1984)].

EXAMPLE 3

Preparation of Ribose by *B. subtilis* RS101

Transformant *B. subtilis* RS101 obtained in Example 2 was inoculated onto 20 ml of a medium comprising 2% sorbitol, 2% corn steep liquor, 0.1% $KH_2PO_4$, 0.3% $K_2HPO_4$ and 50 μg/ml L-tryptophan (pH 7.2), and cultivated with shaking at 37° C. for 16 hours. Then, 1 ml of the resultant culture broth was transferred to 20 ml of a medium containing 16% glucose (separately sterilized), 2% corn steep liquor, 0.5% $(NH_4)_2SO_4$, 1.5% $CaCO_3$ and 50 μg/ml L-tryptophan, and cultivated with shaking at 37° C. for 72 hours. After completion of cultivation, the accumulated amount of D-ribose was determined on high performance liquid chromatography. This result revealed that 62 mg/ml of D-ribose was accumulated. When *B. subtilis* TK103 was cultivated under the same conditions, the amount of D-ribose accumulated in the culture broth after completion of cultivation was only 39 mg/ml.

What is claimed is:

1. A microorganism belonging to the genus Bacillus having D-ribose producing ability transformed with a DNA segment comprising a gluconate operon which is modified so as to highly express the gluconate operon in said microorganism, wherein the modification of the gluconate operon comprises deleting or inactivating the gntR gene.

2. A microorganism belonging to the genus Bacillus having D-ribose producing ability transformed with a DNA segment comprising a gluconate operon which is modified so as to highly express the gluconate operon in said microorganism, wherein the modification of the gluconate operon comprises deleting or inactivating a gntR gene, and replacing a promoter of the gluconate operon with another promoter selected from the group consisting of SP, SP01-15, SP01-26, φ29G3b, φ29G2, φ29A1, pur operon, gua B and PI promoters.

3. The microorganism of claim 2, in which said another promoter is said SP promoter.

4. The microorganism of claim 2 which belongs to *Bacillus subtilis*.

5. The microorganism of claim 2, wherein the modification of the gluconate operon comprises deleting the gntR gene.

6. The microorganism of claim 2, wherein the modification of the gluconate operon comprises inactivating the gntR gene.

7. A DNA segment comprising a gluconate operon of a microorganism belonging to the genus Bacillus, which operon is modified so as to highly express said gluconate operon in said microorganism, wherein the modification comprises deleting or inactivating the gntR gene, and replacing a promoter of the gluconate operon with another promoter wherein said another promoter is selected from the group consisting of SP, SP01-15, SP01-26, φ29G3b, φ29G2, φ29A1, pur operon, gua B and PI promoters.

8. The DNA segment of claim 7, in which said promoter is SP promoter.

9. The DNA segment of claim 7 wherein the microorganism belongs to *Bacillus subtilis*.

10. The DNA segment of claim 7, wherein the modification comprises deleting the gntR gene.

11. The DNA segment of claim 7, wherein the modification comprises inactivating the gntR gene.

12. A vector into which a DNA segment is introduced, which DNA segment comprises a gluconate operon of a microorganism belonging to the genus Bacillus, which operon is modified so as to highly express said gluconate operon in said microorganism, wherein the modification comprises deleting or inactivating the gntR gene, an replacing a promoter of the gluconate operon with another promoter wherein said another promoter is selected from the group consisting of SP, SP01-15, SP01-26, φ29G3b, φ29A1, pur operon, gua B and PI promoters.

13. The vector of claim 12, in which said another promoter is said SP promoter.

14. The vector of claim 12 wherein the microorganism belongs to the genus *Bacillus subtilis*.

15. The vector of claim 12, wherein the modification comprises deleting the gntR gene.

16. The vector of claim 12, wherein the modification comprises inactivating the gntR gene.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: rRNA ( x i ) SEQUENCE DESCRIPTION: SEQ ID NO:1:

CCUCCUUUCU    10

( 2 ) INFORMATION FOR SEQ ID NO:2:

( i ) SEQUENCE CHARACTERISTICS:
      ( A ) LENGTH: 46 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:2:

AAAAGGTATT GACTTTCCCT ACAGGGTGTG TAATAATTTA TATACA    46

( 2 ) INFORMATION FOR SEQ ID NO:3:

( i ) SEQUENCE CHARACTERISTICS:
      ( A ) LENGTH: 46 base pairs (B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:3:

AAAAGTTGTT GACTTTATCT ACAAGGTGTG GCATAATAAT CTTAAC 46

(2) INFORMATION FOR SEQ ID NO:4:

(i) SEQUENCE CHARACTERISTICS:
(A) LENGTH: 46 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:4:

GAAAAGTGTT GAAAATTGTC GAACAGGGTG ATATAATAAA AGAGTA 46

(2) INFORMATION FOR SEQ ID NO:5:

(i) SEQUENCE CHARACTERISTICS:
(A) LENGTH: 47 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:5:

GAAAAGGGTA GACAAACTAT CGTTTAACAT GTTATACTAT AATAGAA 47

(2) INFORMATION FOR SEQ ID NO:6:

(i) SEQUENCE CHARACTERISTICS:
(A) LENGTH: 46 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:6:

ATTAATGTTT GACAACTATT ACAGAGTATG CTATAATGGT AGTATC 46

(2) INFORMATION FOR SEQ ID NO:7:

(i) SEQUENCE CHARACTERISTICS:
(A) LENGTH: 46 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:7:

TAATATCGTT GACATTATCC ATGTCCGTTG TTAAGATAAA CATGAA 46

(2) INFORMATION FOR SEQ ID NO:8:

(i) SEQUENCE CHARACTERISTICS:
(A) LENGTH: 46 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:8:

```
CCGCTTCCTT GACATGCTCT TGGCTAGTTG ATAATCAACA TATAAT                      46
```

( 2 ) INFORMATION FOR SEQ ID NO:9:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
AAAACATTTA CTCCATGGAA AATGATGATA GATTAATTTT TAA                          43
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

```
AGCTACGAAA GCTCATGTCT CGGCGCCTGC                                         30
```